United States Patent [19]

Fitzpatrick et al.

[11] Patent Number: 5,099,208
[45] Date of Patent: Mar. 24, 1992

[54] METHOD FOR MAGNETIC RESONANCE IMAGING AND RELATED APPARATUS

[75] Inventors: J. M. Fitzpatrick; Hsuan Chang, both of Nashville, Tenn.

[73] Assignee: Vanderbilt University, Nashville, Tenn.

[21] Appl. No.: 417,516

[22] Filed: Oct. 5, 1989

[51] Int. Cl.⁵ ............................................ G01R 33/20
[52] U.S. Cl. ...................................................... 324/312
[58] Field of Search .......................... 324/307, 309, 312; 128/653 A, 653 SC

[56] References Cited

U.S. PATENT DOCUMENTS

| | | | |
|---|---|---|---|
| 4,315,216 | 2/1982 | Clow et al. | 324/309 |
| 4,618,978 | 10/1986 | Cosman | 324/309 |
| 4,620,154 | 10/1986 | Inouye | 324/309 |
| 4,714,885 | 12/1987 | Paltiel et al. | 324/312 |
| 4,727,326 | 2/1988 | Kaplan et al. | 324/309 |
| 4,728,890 | 3/1988 | Pattany et al. | 324/309 |
| 4,733,188 | 3/1988 | Sekihara et al. | 324/312 |
| 4,740,749 | 4/1988 | Yamamoto et al. | 324/309 |
| 4,745,364 | 5/1988 | Hatanaka | 324/309 |
| 4,766,381 | 8/1988 | Conturo et al. | 324/309 |
| 4,818,941 | 4/1989 | McKinnon | 324/309 |
| 4,823,085 | 4/1989 | Fuderer et al. | 324/312 |
| 4,825,159 | 4/1989 | Oppelt et al. | 324/309 |
| 4,920,314 | 4/1990 | Satoh | 324/312 |

*Primary Examiner*—Michael J. Tokar
*Attorney, Agent, or Firm*—Arnold B. Silverman; Rita M. Rooney

[57] ABSTRACT

An improved method and related apparatus is provided for magnetic resonance imaging with distortions due to magnetic field inhomogeneities and subject susceptibility corrected. The method includes providing a subject positioned within a main magnetic field, a source of RF signals, a receiver for receiving signals emitted from the subject responsive to the RF pulses and emitting responsive output signals, a computer for receiving the output signals from the receiver and establishing image information related thereto and a visual display for displaying images obtained from the image information. The improved method includes performing a first image generating sequence including generating a 90° RF pulse while simultaneously applying a first slice selection gradient, a phase-encoding gradient and subsequently applying a first preparation gradient after which a 180° refocussing pulse is generated. Subsequently a first read-out gradient is generated while the echo signal is read by the receiver. The sequences is repeated a sufficient number of times to create a first volume image. A second image generating sequence is performed which is similar to the first except that the slice selection gradient, the preparation gradient and the read-out gradient are changed by the same ratio. The second image thereby generated is combined by a computer to create a third, nondistorted image, which may then be delivered to a visual display or other application.

23 Claims, 6 Drawing Sheets

METHOD FOR MAGNETIC RESONANCE IMAGING AND RELATED APPARATUS

BACKGROUND OF THE INVENTION

1. Field Of The Invention

This invention relates to nuclear magnetic resonance imaging and, in particular, it relates to an improved method and apparatus for correcting inaccuracies in magnetic resonance images which result from inhomogeneities in the magnetic field, and inhomogeneities that are produced by the subject, as well as by the imaging instrument.

2. Background Information

The advantageous use of noninvasive and nondestructive test procedures has long been known in both medicine and industrial applications. In respect of medical uses, it has also been known that limiting a patient's exposure to potentially damaging X-ray radiation may advantageously be accomplished through the use of other non-invasive imaging procedures such as, for example, ultrasound imaging and magnetic resonance imaging.

In a general sense, magnetic resonance imaging (MRI) involves providing bursts of radio frequency energy on a specimen positioned in a main magnetic field in order to induce responsive emission of magnetic radiation from the hydrogen nuclei or other nuclei. The emitted signal may be detected in such a manner as to provide information as to the intensity of the response and the spatial origin of the nuclei emitting the responsive magnetic signal. In general, the imaging may be performed in a slice, or plane or multiple or three-dimensional volume with information corresponding to the responsively emitted magnetic radiation being received by a computer which stores the information in the form of numbers corresponding to the intensity of the signal. The Pixel value is established in the computer by employing Fourier Transformation which converts the signal amplitude as a function of time to signal amplitude as a function of frequency. The signals are stored in the computer and may be delivered with or without enhancement to a video screen display such as a cathode-ray tube, for example, wherein the image created by the computer output will be presented through black and white presentations varying in intensity or color presentations varying in hue and intensity (and "saturation" or amount of "white" mixed in).

It has been known that magnetic resonance image intensity is dependent upon certain inherent physical properties of the tissues being investigated and timing intervals chosen by the user of the equipment. The physical properties of the tissues include the hydrogen density or density of the sensitive nucleus and two time factors which are known as $T_1$ and $T_2$. $T_1$ which is also known as "$T_1$ relaxation" is a measure of how long it takes the sample to regain its potential to produce a signal after a first pulse has caused it to respond to the pulsed RF excitation. This is sometimes considered as the time required to restore the longitudinal magnetization. $T_2$ or "$T_2$ relaxation" is a measure of the amount of time required for the magnetic resonance signal emitted by the radio frequency energy-excited proton to ideally dissipate to a point where it is generally imperceptible. At equilibrium, the transverse component of magnetization is at zero and the longitudinal component is equal to the initial magnetization. Decay to the former equilibrium is governed by the $T_2$ relaxation and decay to the latter equilibrium is governed by the $T_1$ relaxation. By properly selecting the timing intervals, the differences in hydrogen density or density of the sensitive nucleus, $T_1$, and $T_2$ values produce a difference in image intensity.

It has been known to use spin echo techniques in magnetic resonance imaging. In conventional spin echo imaging procedures, after an initial 90 degree pulse or general alpha-degree pulse, there are at predetermined intervals a 180 degree RF pulse and magnet which serve to refocus the transverse magnetization after the signal from the nuclei disappears to thereby cause the signal to reappear. The regenerated signal is referred to as a "spin echo". To the extent to which $T_2$ relaxation has occurred prior to the generated spin echo, that portion of the signal is reduced.

As noted hereinbefore, utilization of nuclear magnetic resonance (hereinafter referred to as "NMR"), and particularly to forming an image utilizing NMR has become widespread in recent years. Although it has broad application, NMR imaging has become increasingly important in the medical arena where it is used to noninvasively inspect various parts of the human body.

It has been known to employ stereotactic procedures in neurosurgery applications. During such procedures, a rigid, three-dimensional reference frame is attached to the skull before and during the acquisition of volumetric images. The frame is used to guide the surgeon to the target area of the brain requiring surgery. The guidance is based on precise image measurements of geometrical coordinates of the target relative to the frame. The precision is such that the term "stereotactic" customarily implies ultimate precisional accuracy during surgery within one millimeter. Currently, stereotactic guidance is based on computerized tomography ("CT"). MRI has not been used in this field because the images obtained have heretofore suffered from geometric distortions greater than one millimeter which is an unacceptable degree of distortion. However, if such distortion were eliminated, MRI would be preferable to CT in many applications because it can provide superior soft tissue visualizations.

There have been some attempts to reduce distortion in MRI. For example U.S. Pat. No. 4,740,749 discloses an NMR imaging method based upon the modified spin warp method, but the method employs repeating the measurement of signals many times in order to decrease noise in the image. The method involves varying the intensity of the field or the time interval of the phase encoding gradients. The technique, however, is not satisfactory to reduce field inhomogeneities to the level of accuracy achieved by the present invention.

U.S. Pat. No. 4,728,890 discloses a motion artifact suppression technique involving rephasing the magnetic resonance signal components from moving tissues. The method includes a sequence during which several motion desensitization pulses are applied, and an algorithm for reconstruction of the image is provided.

U.S. Pat. No. 4,315,216 discloses an imaging system which applies magnetic fields to the body being examined nd which utilizes pulses which are not square pulses, instead, the pulse would perhaps be a distorted sinusoid. The resonance signal is sampled during that pulse.

U.S. Pat. No. 4,620,154 involves generating one image using a saturation-recovery method and generating a second image using an inversion-recovery method to create a third image from a ratio of the first and second images.

U.S. Pat. No. 4,825,159 discloses generating NMR images using a sequence involving reversal of gradient directions during successive sequences. However, it is not directed towards reduction of field inhomogeneities as is one of the objects of the present invention; instead, it is directed towards simultaneously obtaining two different images having differing diagnostic value.

U.S. Pat. No. 4,714,885 discloses an MRI technique allowing the operator to acquire data in a single scan which can be used for separate imaging of two spectrocomponents or for reducing chemical shift artifacts.

U.S. Pat. No. 4,818,941 discloses an improved imaging method using the spin warp technique involving a variation in the gradient field during sequence repetition. It involves the use of only one high frequency pulse during each sequence. In the next sequence, the pulse is shifted with respect to its distance from the echo signal. This method is directed towards generation of water and fat images and not towards the reduction in field inhomogeneities in the imaging technique.

U.S. Pat. No. 4,823,085 involves an imaging method which relates to the elimination of phase error in a single scan of the body. U.S. Pat. No. 4,745,364 also discloses a phase error correction technique.

U.S. Pat. No. 4,727,326 involves acquiring a first image in accordance with conventional methods and after slightly varying the orientater magnetic field, another image is acquired, then an image of a third type is formed by representing relative variations of the relaxation times between the first and the second image. This invention is directed towards constructing an image by discrimination of the intrinsic parameters of the tissues being examined.

U.S. Pat. No. 4,733,188 discloses an imaging method which involves repeating a sequence including changing the phase of a second gradient magnetic field which is periodically inverted in sense.

These patents do not achieve the accuracy of image which is achieved by the present invention in the time period or to the level of accuracy achieved by the present invention.

In spite of the foregoing attempts there remains a need for an improved method and related apparatus for providing MRI images which are nondistorted and which may be used during stereotactic neurosurgery and other procedures requiring extreme accuracy.

SUMMARY OF THE INVENTION

As used herein, the terms "subject," "specimen" or "examination subject" shall refer to any object placed in the main magnetic field for imaging and shall expressly include but not be limited to members of the animal kingdom including humans, test specimens such as biological tissue, for example, removed from such members of the animal kingdom and inanimate objects which may be imaged by NMR or contain water or sources of other sensitive nuclei.

The present invention provides an improved method of magnetic resonance imaging and a technique for correction of distortion due to field inhomogeneities and object susceptibility. A specimen is positioned within a main magnetic field and a source of RF signals in the form of pulses is positioned adjacent to the specimen. Receiver means for receiving signals emitted from the specimen responsive to the imposed RF pulses are positioned adjacent to the subject and the receiver means emits responsive output signals upon receipt of the subject responses. Computer means receive the output signals from the receiver means and establish image information related thereto. Information regarding several images is generated and stored. The image information may be provided directly after storage to visual display means for displaying images from the image information received from the computer.

The technique of the present invention includes providing a static magnetic field within which the subject is disposed A 90° RF pulse is generated while simultaneously a slice selection gradient in a first direction is applied. Subsequently, a phase-encoding gradient is applied in a second direction after which a preparation gradient is applied in a third direction for a certain period of time. An 180° pulse is then applied in a conventional manner. During the application of a read-out gradient in the third direction, the NMR signal corresponding to a first image is measured and stored in a computer means. This sequence is repeated N times to obtain the information representative of an image for one slice of the subject, where N may be preferably 128, 256 or 512.

Having stored the information, regarding a first image, information is then obtained for a second image by performing the same sequence with the exception that the slice selection gradient is changed such that the signed ratio between this gradient and that used for the first image is $\alpha$. In the exemplary case $\alpha = -1$, meaning that it is in the opposite direction as the slice selection gradient for the first image in the exemplary case. In addition, the read-out gradient is also changed by the same factor. This procedure is used to generate information representative of a second image.

The sequences are repeated for a number of slices and the information is stored in respect of the first and second images until enough information is obtained to construct two volume images. The information so obtained is subjected to two dimensional Fourier Transformation to generate the two images.

The invention involves the distortion present in the image being collinear at all points of the image. Based upon the mathematical relationship describing this phenomenon, which is described in detail hereinafter, the two acquired images are combined to create a third image which is free of geometrical and intensity distortions.

It is an object of this invention to provide a method of magnetic resonance imaging which corrects for intensity distortions due to magnetic imperfections, object susceptibility, and magnetic variables in the equipment used.

It is another object of the invention to generate two images and combine those two images to produce a third, undistorted magnetic resonance image.

It is another object of the invention to produce the undistorted image in a suitably short period of time.

It is another object of the invention to produce an image sufficiently free of distortion that it can be safely and reliably used to guide a surgeon during performance of stereotactic neurosurgery.

It is another object of the invention to provide a related apparatus system for performing the method of the present invention.

It is a further object of the present invention to provide computer means which facilitate accomplishing the objectives of the invention.

It is a further object of the present invention to provide such a system which is compatible with existing equipment and is adapted to be economical to manufacture and use and may be used without significant retraining of individuals conducting the tests.

These and other objects of the present invention will be more fully understood from the following description of the invention with reference to the illustrations appended hereto.

DESCRIPTION OF THE PREFERRED EMBODIMENTS

Figure 1:
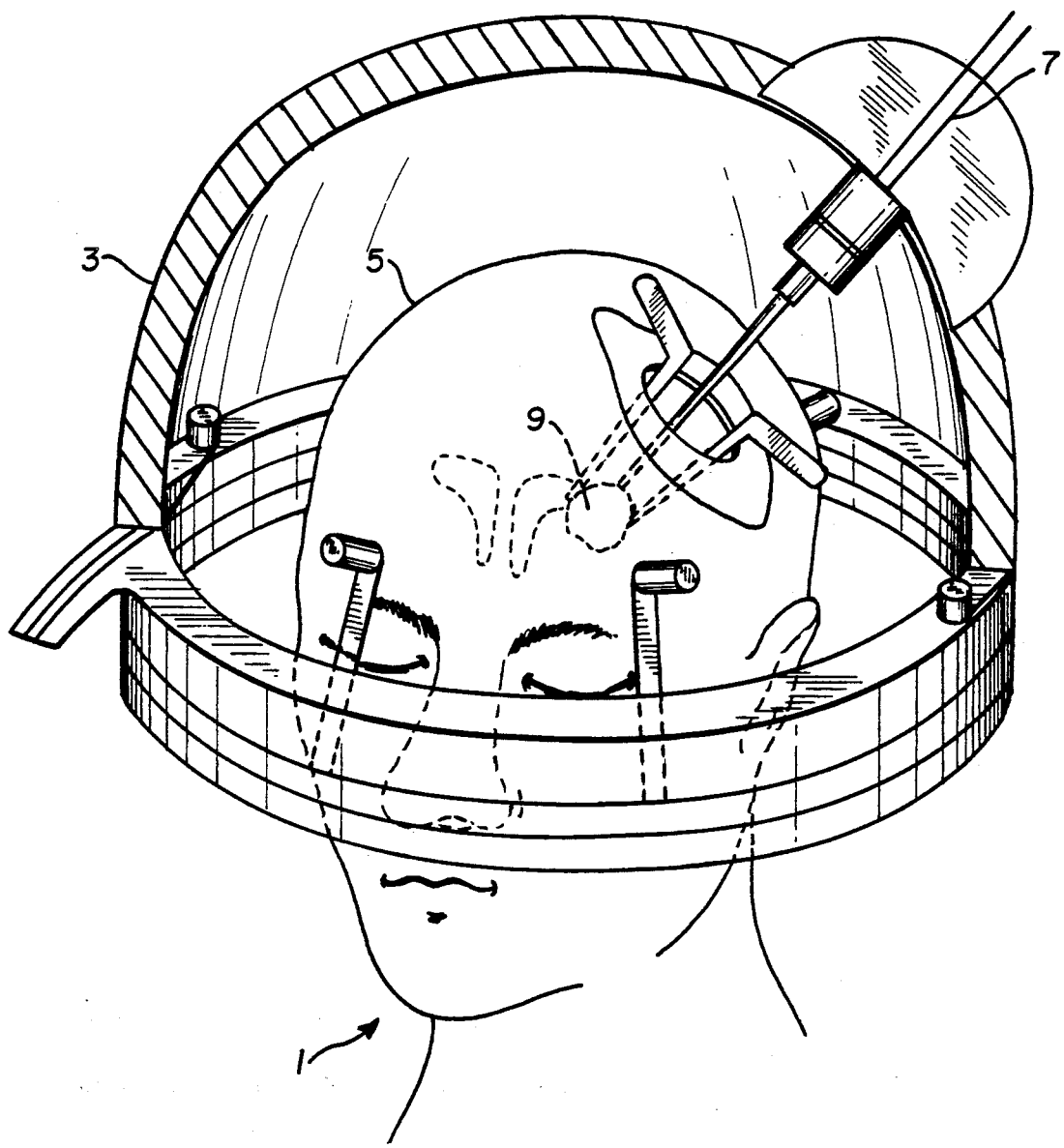
FIG. 1 is a schematic view of a stereotactic frame attached to a patient's head for purposes of performing stereotactic surgery during which the method and apparatus of the present invention may be employed.

FIG. 1 shows a patient 1 who is undergoing neurosurgery on the brain. The three-dimensional reference frame 3 is placed upon the patient's head 5 to guide the surgeon in using the surgical instrument 7 to the area of the brain 9 of interest in the application.

The three-dimensional reference frame 3 is provided with a grid (not shown) which would be superimposed upon the MRI image to be taken of the region of the brain 9 of interest in the application . The surgeon would refer to a visual display of an image and would locate by reference to that image, the area of the brain to be operated upon. As noted hereinbefore, this image must be accurate to within 1 millimeter.

Previous MRI techniques, however, have produced distorted images due to several factors such as, inhomogeneities in the static field and in the susceptibility of the subject to magnetization. In addition, there is a degree of variation in composition and structure of the brain and hence in the inhomogeneity in susceptibility between different subjects. The primary problem is due to inhomogeneities in the static magnetic fields caused by both magnet imperfections and nonuniform magnetization of the patient. This invention is directed towards correcting these latter inhomogeneity problems. More particularly, the invention is predicated upon the fact that spatial inhomogeneity in the static magnetic field produced for MRI produces geometrical image distortion. The effect arises because the position of a proton is deduced from its processional frequency and this frequency is determined by the local magnetic field. When a spatial variation in the field is purposefully produced by the addition of precisely controlled magnetic field gradients to a homogeneous static field, the relationship between frequency and spatial position is known. However, if a spurious, unplanned perturbation in the static field is present at the position of a given proton, its frequency will be shifted to a frequency expected at some other position, and it will be assigned to that position when the image is reconstructed which would be erroneous. The size of the shift, in the x direction, for example, depends on the ratio of the erroneous variation in the field to the magnitude of the gradient in that direction, $$\Delta x = \frac{\Delta B}{G_x} \qquad \text{Eq. (1)}$$

where $\Delta B$ is the field variation and $G_x$ is the gradient. The effect is depicted schematically in FIG. 1A.

Figure 1A:
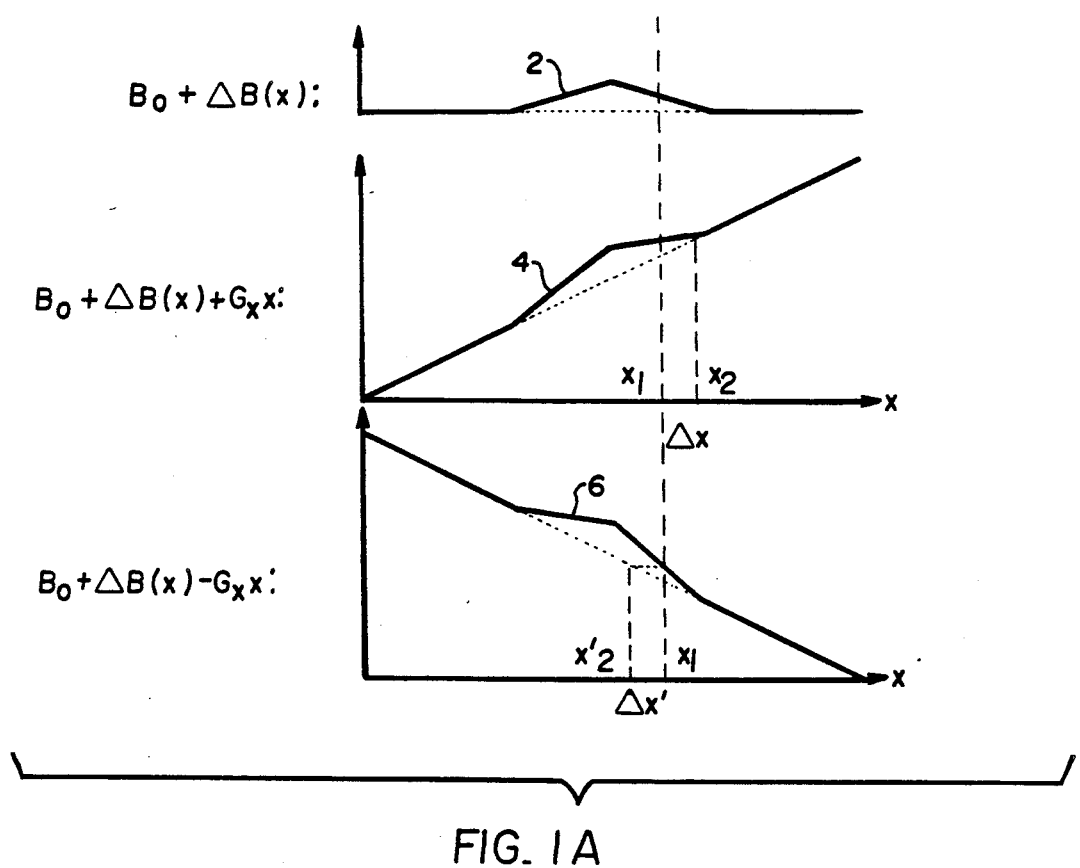
FIG. 1A is a graph of shift in position as it relates to field variation and gradient for three different sets of conditions.

As shown in curve 2 of FIG. 1A, the effect of a triangularly shaped static field perturbation is shown for a proton located at $x_1$. The perturbation shown in curve 2 combines with the linear gradient to produce the nonlinear field shown in curve 4. The processional frequency of a proton at $x_1$ corresponds erroneously to the frequency expected at $x_2 = x_1 + \Delta x$, where the subscript 1 denotes the actual position, and the subscript 2 denotes the distorted position.

In general the size of the field perturbation can be expected to vary with position in the image. As a result, the shift $\Delta x$ varies with position as well. Such variation can result in a secondary effect: the image intensity is not only shifted from one point to another, but is also changed in value. This effect, which occurs wherever the image is stretched or compressed, is quantified by the Jacobian of the geometrical mapping and is discussed hereinafter.

Substituting Equation (1) for $\Delta x$, it can be seen that the distortion in the read-out direction (the x direction as explained hereinafter) may be described as follows:

$$x_2 = x_1 + \frac{\Delta B}{G_x} \qquad \text{Eq. (2)}$$

Similarly, the distortion in the slice selection direction (which is chosen to be the y direction, as explained hereinafter) may be described as follows:

$$y_2 = y_1 + \frac{\Delta B}{G_y} \qquad \text{Eq. (3)}$$

Figure 4:
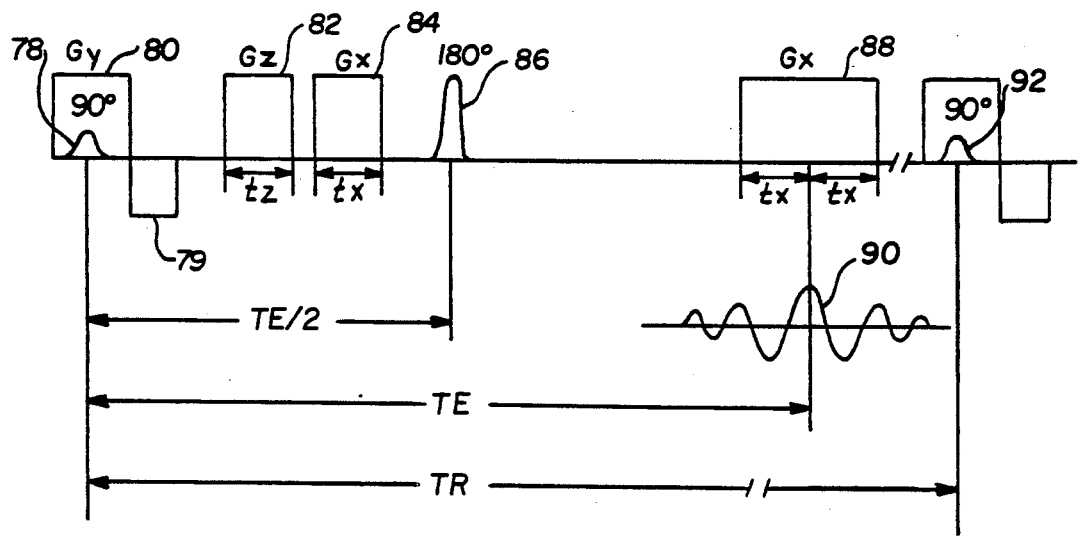
FIG. 4 shows an example of a waveform of the preferred pulse and gradient sequence for slice selection, phase-encoding and read-out to be used in the acquisition of the first image to be used in accordance with the teachings of the present invention.
Figure 5:
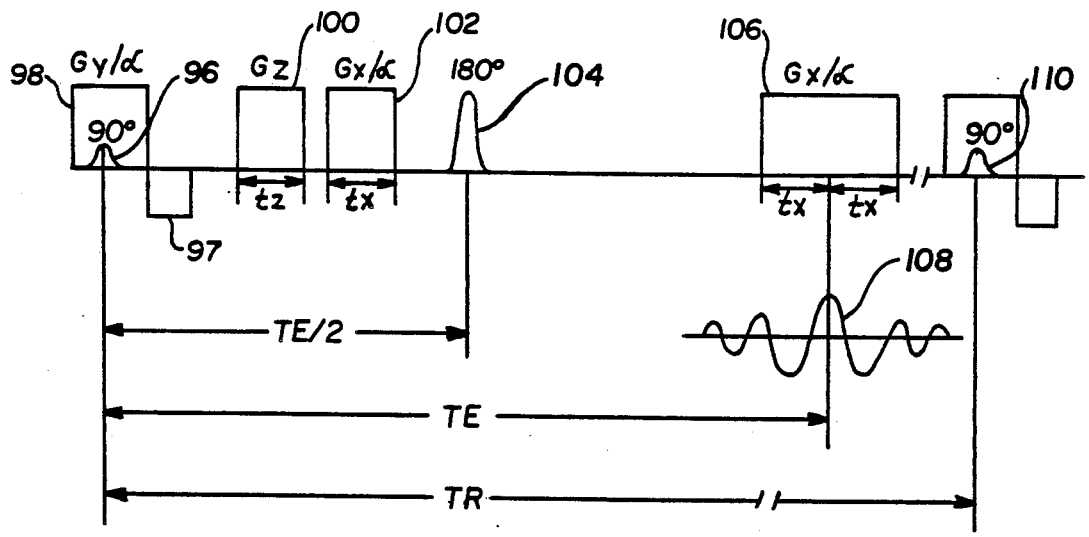
FIG. 5 shows an example of a waveform of the preferred pulse and gradient sequence for slice selection, phase-encoding, and read-out to be used in the acquisition of the second image to be used in accordance with the teachings of the present invention.

There is no distortion in the phase-encoding direction (the z direction), so that $z_1 = z_2 = z_o$, because for spin echo imaging phase encoding is insensitive to constant errors in the magnetic field so long as $t_z$ is constant (FIGS. 4 and 5).

Comparing Equations (2) and (3) shows that throughout the three-dimensional image the motion lies along a line parallel to the vector $g = (1/G_x, 1/G_y, 0)$. Rotating the coordinate system so that the new x-axis lies along this line, it can be seen that the transformation is reduced to one dimension:

$$x_2 = x_1 + g\Delta B, \qquad (4)$$

where $g = \sqrt{G_x^2 + G_y^2}/(G_x G_y)$. The distorted three-dimensional image, $i_2$, in this new coordinate system has the following relationship to the undistorted image, where "image" as used in this context means the modulus of the complex image produced in the presence of inhomogeneities:

$$i_2(x_2, y_1, z_o) = \frac{i_1(x_1, y_1, z_o)}{J(x_1, y_1, z_o)} \qquad \text{Eq. (5)}$$

where $J = dx_2/dx_1$. Because of the appearance of J in the denominator, the image value is not only shifted spatially according to Equation (4), but also changed in intensity. This change can be seen as a darkening or lightening of the image and it appears where ever the geometrical distortion results in a stretching or compression. This change is also corrected by the present invention.

In accordance with the method of the present invention as explained in full hereinafter, a first image is acquired and is described in accordance with Equation (5).

Now, a second volume image is acquired with both the slice selection and read-out gradients changed. Using a slice selection gradient $G_y'$, the second read-out gradient is $G_x'$. The present invention utilizes the following relationship: $G_x/G'_x = G_y/G'_y = \alpha$ where $\alpha$ is a signed value. In this image all geometrical shifts—those due to magnet imperfections, those due to patient's magnetization, and chemical shifts—are changed. The effect is depicted schematically in curve 6 of FIG. 1A where $\alpha = -1$, that is, the gradients are of opposite polarity in this exemplary case. There it can be seen that the point $x_1$, formerly shifted to the right to $x_2$, is now shifted left to $x'_2$. By examining the slopes it can be seen that $\Delta x' = \Delta x' = (x_2 - x'_2)/2$. It can also be seen that the actual position $x_1$ of the exemplary case is the average of the two apparent positions $x_2$ and $x'_2$, $(x_2 + x'_2)/2$. Thus, by means of the acquisition of two images with, for example, gradient reversal, the imaged object provides a self reference: the distortion in one image is mirrored in the other. For the general case, $$x_1 = \frac{\alpha x_2 - x_2'}{\alpha - 1}$$

Substituting the relationship $J = dx_2/dx_1$, into the Equation (5) produces $$dx_2/dx_1 = i_1(x_1, y_1, z_o)/i_2(x_2, y_1, z_o)$$

For the second image ($i'_2$) a similar equation exists:

$$dx'_2/dx_1 = i_1(x_1, y_1, z_o)/i'_2(x'_2, y_1, z_o)$$

By combining these two equations, the following equation relates to the two distorted images, $$dx'_2/dx_2 = i_2(x_2, y_1, z_o)/i'_2(x'_2, y_1, z_o)$$

This is an ordinary, first order differential equation which can be solved by numerical integration techniques known to those skilled in the art to produce a mapping between points $x_2$ and $x'_2$ in the two distorted images, from which the undistorted position can be determined by means of $x_1 = (\alpha x_2 - x'_2)/(\alpha - 1)$. Forming derivatives with respect to $x_1$ from this equation for $x_1$ it may be found that:

$$\alpha \frac{dx_2}{dx_1} - \frac{dx'_2}{dx_1} = \alpha - 1 \qquad \text{Eq. (9)}$$

By combining this equation with Equations (6) and (7) an expression for the undistorted image from a combination of the two distorted images can be derived:

$$i_1(x_1, y_1, z_o) = \frac{(\alpha - 1)i_2(x_2, y_1, z_o)i'_2(x'_2, y_1, z_o)}{\alpha\, i'_2(x'_2, y_1, z_o) - i_2(x_2, y_1, z_o)} \qquad \text{Eq. (10)}$$

where $x_1 = (\alpha x_2 - x'_2)/(\alpha - 1)$. The resulting image is free of both geometrical distortion and intensity distortion.

The size of the inhomogeneities that this technique can accommodate is limited only by the requirement that the Jacobian be non-zero. This requirement is equivalent to the statement that the mapping from one image space to another must remain one-to-one. IN regions for which the mapping is not one-to-one there will be an overlap. The signal from two different points in object space will add together into one point in image space. The fundamental requirement that the mapping be one-to-one, will be satisfied, as can be seen from Equation (4) and the expression of J given above, as long as $$\left| \frac{\partial \Delta B}{\partial x} \right| < |G_x G_y| / \sqrt{G_x^2 + G_y^2} \qquad \text{Eq. (11)}$$

which is a relationship between field variation and the gradients $G_x$ and $G_y$.

Figure 2:
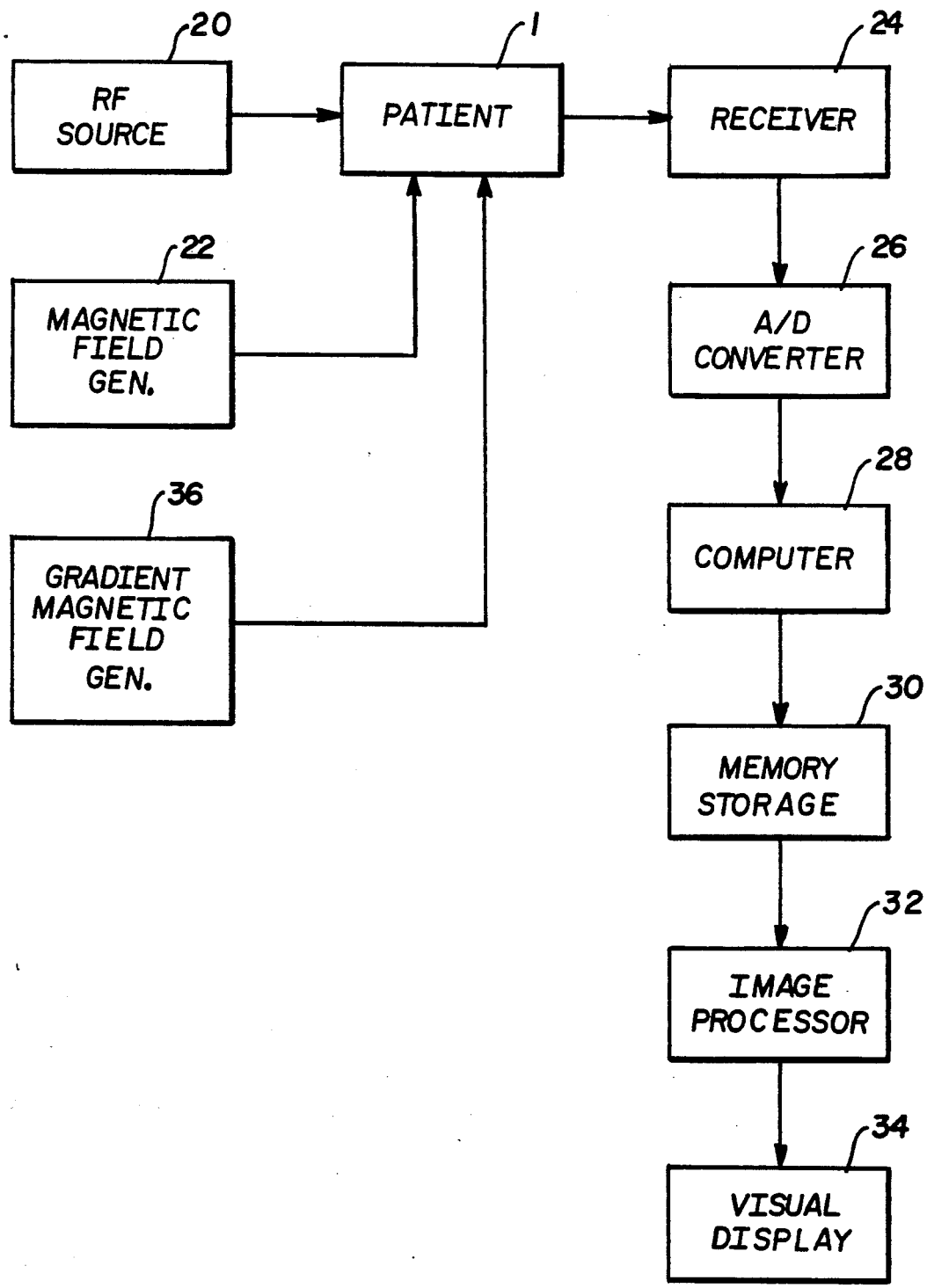
FIG. 2 is a schematic illustration of an exemplary magnetic resonance imaging system in accordance with the present invention.

. A schematic illustration of the apparatus of the present invention which exploits the above-described relationship is shown in FIG. 2. A conventional RF source 20 provides a pulse of radio frequency energy to the subject in the form of a patient 1 placed in a magnetic field (which is on continuously). The subject is generally aligned with the main magnetic field and the RF pulses are imposed perpendicular thereto. The main magnetic field may be generated by a conventional magnetic field generator 22 and is generally perpendicular to the radio frequency (RF) field. This results in excitation of the nuclei within the area or volume to be imaged and causes responsive emission of magnetic energy which is picked up by receiver 24.

The receiver 24 which is conventional may be a coil which has a voltage induced in it as a result of such responsive emission of magnetic energy. As a practical matter, separate coils or identical coils may be employed as the RF source 20 and the receiver 24. The signal emerging from receiver 24 passes through analog-to-digital (A/D) converter 26 and enters computer 28. Within the computer 28, the Fourier Transformation of signals is performed to create the images. As will be readily understood by those skilled in the art, the Fourier Transformation converts the plot of amplitude versus time to a map of the distribution of frequencies by plotting amplitude versus frequency. Further details of the operation of the RF source 20, the main magnetic field generator 22 and the receiver 24 may be found in U.S. Pat. No. 4,766,381 which describes a general system for NMR imaging. The disclosure of U.S. Pat. No. 766,381 is expressly incorporated herein by reference. In the computer 28, the Fourier Transformations are performed in order to establish the intensity values and locations of specific pixels. These values may be stored in a suitable memory storage 30, to be processed as set forth hereinafter by image processor 32 and may be provided to visual display 34 depending upon the application.

Figure 3:
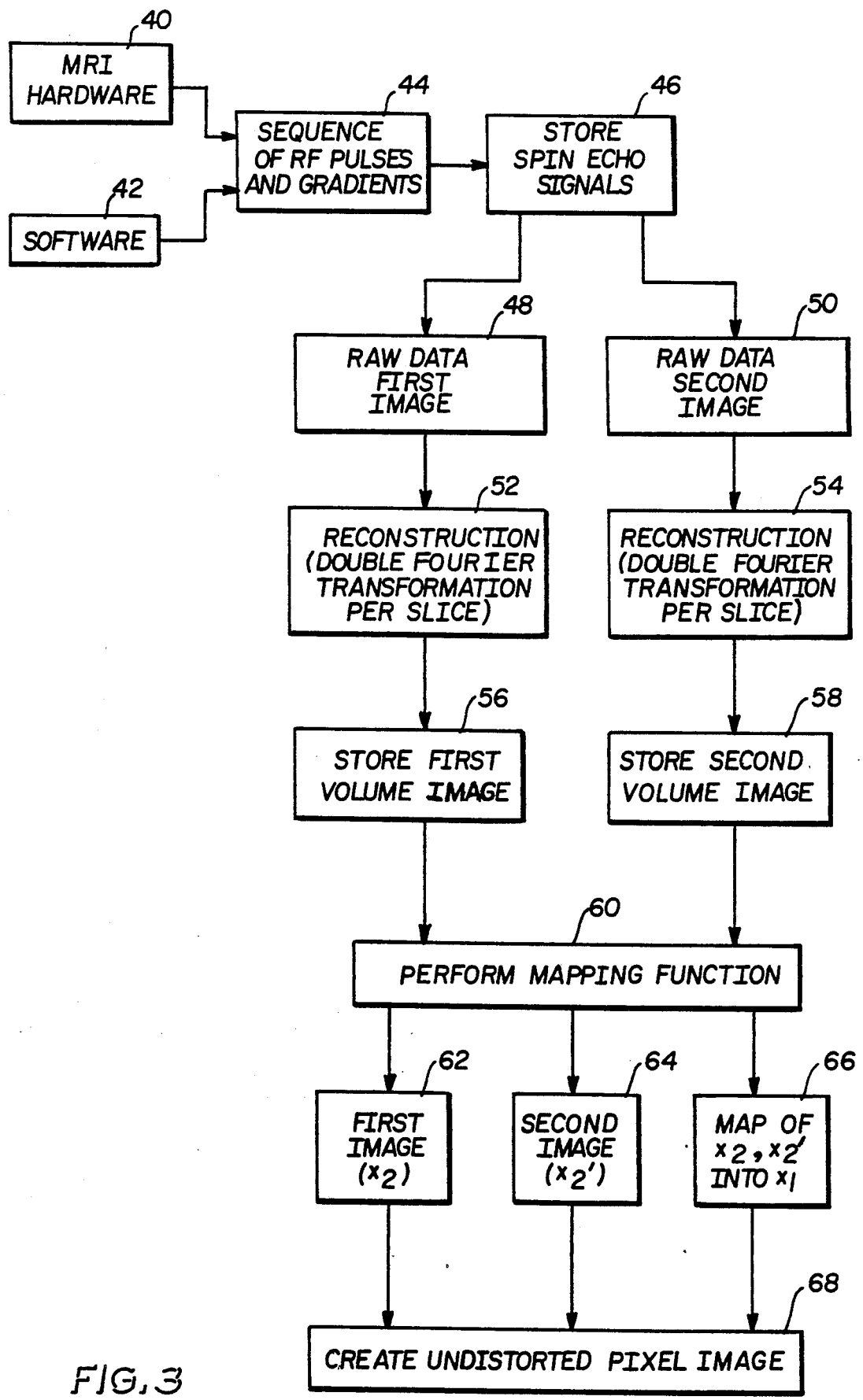
FIG. 3 is a schematic illustration of the data generation and image creation process of the present invention.

Referring to FIGS. 2 and 3 and noting that the subject in FIG. 2 is a patient, reference will be made to an arbitrarily oriented x,y,z gradient coordinate system. Magnetic field gradients are applied along one or more of those axes by gradient magnetic field generator 36 of FIG. 2.

Axis y is normal to the selected slice or slices. Assume imaging of a single transverse slice so that the patient has the longitudinal portions of his or her body aligned with the y-axis along the main magnetic field. The y-axis will also provide a y-axis gradient which has planes of differing magnetic strength oriented in relative spaced relationship, and generally perpendicularly with respect to the y-axis. The y-axis magnetic gradient serves to define the slices of the patient which will be imaged. The main magnetic field will cause nuclear magnetic moments of $1_H$ nuclei (herein referred to as "protons") or other sensitive nuclei in the patient to be aligned parallel or antiparallel thereto in such a manner that the resultant spin vector is oriented generally parallel to the field's longitudinal axis. When pulses of RF energy of a frequency related to the resonant frequency associated with the main magnetic field are applied with an oscillating field oriented perpendicular to the main magnetic field, resonance is established at that frequency so that energy is absorbed in the patient. The resultant spin vectors of the protons are caused to rotate from their orientation along the y-axis toward the plane perpendicular to that axis. If the RF pulse is adequate to rotate the resultant spin vectors through 90 degrees, the pulse is designated a 90 degree pulse. If the RF pulse or general magnetic field pulse is adequate to rotate the resultant spin vectors through 180 degrees, the pulse is termed a 180 degree pulse. After removal of the RF pulse, $T_1$ and $T_2$ relaxation occur. A portion of the absorbed energy is emitted as a signal which can be detected by receiver means 24.

Referring now to FIG. 3, the MRI hardware 40, has associated therewith software 42. This software controls a sequence of RF pulses and gradient pulses 44. This sequence is described in detail hereinbelow. Briefly, the sequence of pulses generates spin echo signals (which are also referred to herein as: NMR signals). The echo signals are stored as designated by reference character 46. 'N' sequences are performed to generate enough raw data 48 to create one slice image for the first volume image. The number of sequences ('N') will preferably be one of 128, 256 or 512. A plurality of slices are then used to create a first volume image.

As discussed hereinbefore, the present invention employs a second volume image and the raw data 50 for that second volume image is generated after the data for the first image is generated.

The reconstruction of the two images may be performed using conventional reconstruction techniques involving double Fourier Transformations for each slice as shown by reference character 52 for the first image and 54 for the second image. The information is then stored as designated by reference characters 56 and 58, respectively. The mapping function discussed hereinbefore whereby each point of the first distorted image which in one dimension may be represented as $x_2$, and each point of the second distorted image which is represented in one dimension as $x'_2$, are subjected to a mapping function designated by reference character 60 whereby $x_2$ and $x'_2$ are mapped into $x_1$—the point corresponding to the corrected image $i_1$. The output of the mapping function is illustrated at reference character 66. The information corresponding to first image 62, the second image 64 and the output of the mapping function 66 is then used in Equation (10) to create all of the points for the corrected image $i_1$, and this is schematically illustrated at reference character 68.

Suitable software code for the mapping function 60 and the creation of the undistorted image from the first image and the second image 68 could be readily developed by one skilled in the art. However, in order to disclose the best mode known to Applicants for practicing the invention, a listing of the currently preferred software along with associated textual descriptions are provided in Appendix A at the end of the Specification and is expressly incorporated herein by reference.

In operation, a subject who may be a patient 1 is placed in a main magnetic field produced by magnetic field generator 22 (FIG. 2). The patient 1 is then subjected to a series of RF pulses produced by RF source 20 and gradient pulses produced by gradient magnetic field generator 36.

Referring now to FIG. 4, a waveform diagram of the above-mentioned pulse-gradient sequence used to generate the first image is shown. An initial 90 degree pulse 78 is supplied to a subject 1 placed in the main magnetic field. Simultaneously, a slice selection gradient pulse $G_y$ (80) is applied. After the 90° pulse and the gradient $G_y$, a y gradient 79, opposite in sign to $G_y$ and somewhat smaller than $G_y$, is applied to compensate for the phase dispersion produced by $G_y$. This is followed by a phase-encoding gradient pulse $G_z$ (82) applied over the time interval $t_z$. A preparation gradient pulse $G_x$ (84) is then applied over time interval $t_x$. A refocussing 180 degree pulse 86 is then applied at time TE/2 (one half of the "echo-time"), and then a read-out gradient pulse $G_x$ (88) is applied. Pulse 86 creates echo 90 at t=TE which is then stored in a suitable storage means such as the memory storage 30 associated with computer 28 (FIG. 2).

This sequence is repeated preferably N times, as discussed hereinbefore, while each time the gradient $G_z$ is sequentially incremented from a negative maximum, up through zero and to a maximum in the positive direction. This produces the raw data 48 (FIG. 3), corresponding to one slice of the first image of the relevant portion of subject 1. Ultimately, after a set of M of such slices are obtained, where M is preferably between about 10 and 50, enough information would be generated to produce a first volume image, and this information is stored as raw data 48 for the first image.

Next, the second volume image is obtained as discussed hereinbefore. Referring to FIG. 5, an initial 90 degree pulse 96 is applied to the subject 1 in the main magnetic field. Simultaneously a slice selection gradient $G_y/\alpha(98)$ is applied. This is followed by a phase-encoding gradient $G_z(100)$ being applied over time interval $t_z$. A preparation gradient $G_x/\alpha(102)$ is then applied over time interval $t_x$. After the preparation gradient $G_x/\alpha(102)$, a 180 degree pulse 104 is generated as a refocussing pulse after which echo signal 108 is produced. The signal 108 is read as read-out gradient $G_x/\alpha(106)$ is applied. As with the first image, the signal (108) is stored in memory storage 30 of computer 28 (FIG. 2). This sequence is repeated N times to generate sufficient data to reconstruct one slice for the second image. Then, further slice information is gathered in an amount sufficient to produce a second volume image.

Preferably the first and second images are not reconstructed until all of the above-described information is obtained and stored. Once such information is obtained and stored, the two images may be reconstructed using conventional reconstruction methods including a two-dimensional inverse Fourier Transformation, after which they are stored. The timing for the sequences is discussed hereinafter.

Once the two images are reconstructed they are then processed by image processor 32 (FIG. 2), which combines the two images using the solution to Equations (8) and (10) discussed hereinbefore and schematically illustrated in FIG. 3, to create the third image. The third image is free of distortion as discussed hereinbefore. The third image can if desired be displayed on a visual display 34 (FIG. 2) and utilized, for example, by a neurosurgeon during the performance of stereotactic neurosurgery because the third image would be an undistorted image having stereotactic precision. This image processing would take typically about 30 seconds using, for example, a Sun 3/260 work station with floating point acceleration.

In the method of the present invention, a static magnetic field would be provided within which a subject 1 is disposed. An RF pulse and gradient pulse sequence utilizing $G_x$ and $G_y$ of FIG. 4 is then applied repeatedly to generate a first slice image and a plurality of slice information is generated sufficient to produce a first volume image. A second distorted image is similarly obtained with gradients $G_x/\alpha$ and $G_y/\alpha$(FIG. 5). Then Equation (8) is solved and is used to solve Equation (10).

The acquisition time per volume is approximately $N \times M \times TR/f$, where TR is the repetition period for the entire cycle and f is the slice interleaving factor. With slice interleaving the cycle for one slice is begun shortly after the signal has been received from another slice. Thus, it is possible to generate and store information from several slices during one repetition period. For example, for a TE ("echo time", which means the time elapsed between the middle of the initialing 90 degree pulse 78 of FIG. 4, for example, to the middle of the peak of the spin echo signal 90) of 22 milliseconds, an interval of 3 milliseconds between the end of the cycle for one slice and the beginning of a cycle for another slice, and TR=500 milliseconds, it is possible to acquire information for as many as 20 slices in one repetition period TR. Thus f could be as large as 20. With f=20 and N=256 in this example the time required to collect one volume image is approximately 2.1 minutes. As two images are required to produce the third undistorted image, the total acquisition time is about 4.2 minutes. In general, the time for acquisition per volume would range between about 0.2 minutes and 12.8 minutes. This is a very acceptable timing in most applications and it represents a significant improvement in timing over the methods of the prior art. The timing may even be faster depending upon the imaging hardware and software used in the application.

EXAMPLE

In order to provide further guidance as to certain preferred practices of the invention, an example of an actual test employing the invention will be considered. The present invention was employed upon a primitive phantom being a two-dimensional grid immersed in water (FIGS. 6A-6F).

Figure 6A:
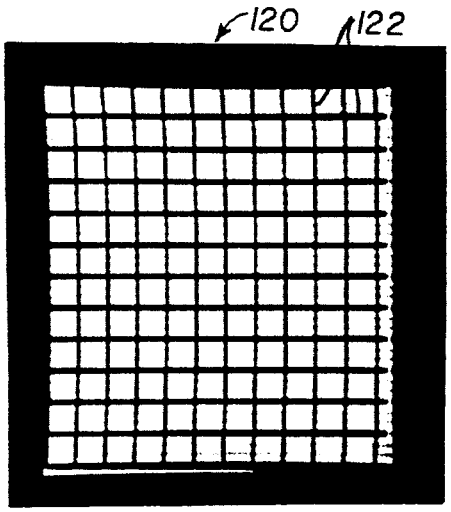
FIG. 6A is a top plan view of an image of a grid produced by nuclear magnetic resonance imaging which image is distorted such that the lines of the grid are bowed toward the right.
Figure 6B:
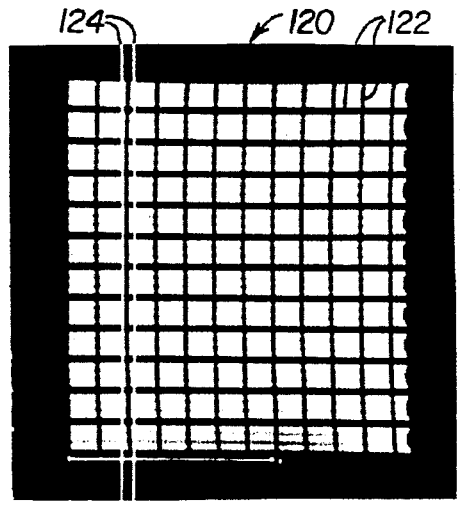
FIG. 6B is the image of the grid of FIG. 6A obtained using the same sequence except the read-out gradient is reversed, or $\alpha = -1$.

Phantom images were acquired on a Siemens 1.5 T Magnetom marketed by Siemens Medical Systems of Iseline, N.J., using the spin echo sequences of FIGS. 4 and 5, with gradient strengths of 2.61 mT/m in the phase-encoding and read-out directions and 1.8 mT/m in the slice selection direction, TE=22 milliseconds, TR=300 milliseconds. The image distortions that were the subject of this investigation arose from magnetic impefiections in the main magnet field generator 22 and from the magnetic susceptibility of the object being imaged, as well as the water. These effects will in general add or subtract from each other, and because they vary independently across the imaged region, the net effect can be complicated. The correction technique of the present invention treats both of these effects in the same way and should simultaneously correct for both. FIGS. 6A-6F show results for the grid phantom. FIGS. 6A and 6B show the unprocessed images. FIG. 6B was acquired with $\alpha = -1$, or the direction of the read-out gradient opposite to that of FIG. 6A. It should be udnerstood that in the full three-dimensional technique the slice selection gradient will be reversed simultaneously, and processing will take place on a set of slices as a single volume image, as described hereinbefore. These preliminary results involve only the distortion in the read-out direction (horizontal in these images) but it should be understood that similar results are attainable for three-dimensional images.

The grid phantom 120 is a two-dimensional array of interlocking plastic strips 122 immersed in water. The bowing to the right, noticeable in FIG. 6A, and to the left in FIG. 6B, is caused by geometrical distortion due both to magnet imperfections and the susceptibility of the water in which the grid is immersed. The distortion lies along the read-out gradient, which is horizontal in the images shown. Distortion can be expected in the slice selection direction as well, but it is not visible with a two-dimensional phantom. There is no geometrical distortion along the phase-encoding direction, which is vertical in all images. The two white, vertical lines 124 are included in FIG. 6B as references, to show the extent of the bowing. They are drawn so as to completely enclose one vertical black line. By comparison, the white lines 126 in FIG. 6E, where a corrected image is shown, are closer together, indicating that the corrected image has been rendered more accurate.

Figure 6C:
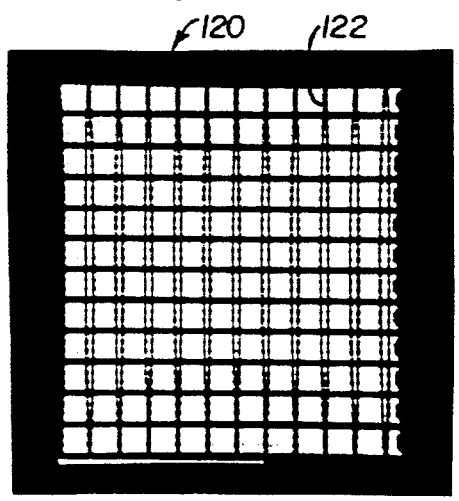
FIG. 6C is an image in which the image of FIG. 6B is superimposed upon the image of FIG. 6A.
Figure 6D:
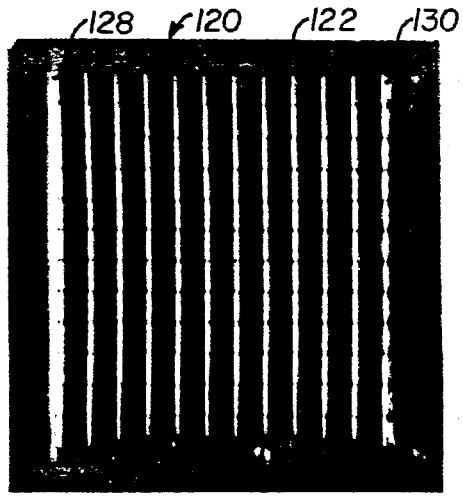
FIG. 6D is the difference of the images of FIGS. 6A and 6B.

The composite of these two images, shown in FIG. 6C, reveals the extent of the distortion. There it can be seen that the distortion in FIGS. 6A and 6B is approximately equal, but in opposite directions. The distortion is greatest at the edges, where the total difference in position is approximately 5.8 mm. This difference is easier to see in FIG. 6D, where the difference of the images in FIGS. 6A and 6B is shown. In FIG. 6D the relatively wide, white vertical bow-shaped stripe on the left 128 and the vertical, black "string of beads" on the right 130 show the relative distortion at the edges. Dividing this distortion by two, since the total relative distortion is the sum of two equal and opposite absolute distortions, the positional error in either of the images of FIGS. 6A and 6B is 2.9 mm near the edges of those images. The error decreases to about half this size near the center.

Figure 6E:
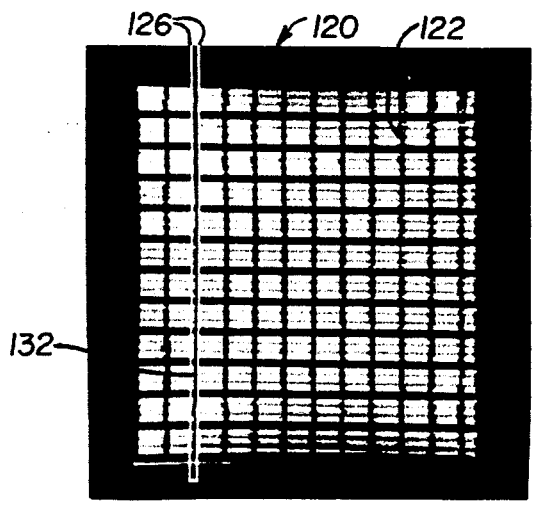
FIG. 6E is the corrected image of the grid of FIGS. 6A and 6B, which was corrected using the method and apparatus of the present invention.

An error of the magnitude shown in the uncorrected images of FIGS. 6A and 6B is too large for stereotactic procedures, which require images accurate to one millimeter or better. Using the technique of the present invention, the two images of FIGS. 6A and 6B may be processed to produce an image with greatly reduced geometrical distortion. That image is produced by the apparatus and method described hereinbefore, including the procedure involving reversal of the slice selection and read-out gradients. The processed image is shown in FIG. 6E. The two white vertical lines 126, corresponding to the similar lines 124 in FIG. 6B, show that the enclosed black line 132 is now straight. The slight bowing of the white lines 126 is due entirely to the curvature of the display screen from which the photographs were taken. At the resolution of these images, which is 1.17 mm per pixel, no remaining global geometrical distortion can be detected, but there is some obvious, noisy horizontal displacements that were not present in the unprocessed images. This noise is introduced by the numerical nature of the processing. These jagged displacements are in almost all cases less than or equal to one pixel, or 1.17 mm, but they should be removed by employing improved algorithms for numerical integration, which would be readily understood by those skilled in the art.

Figure 6F:
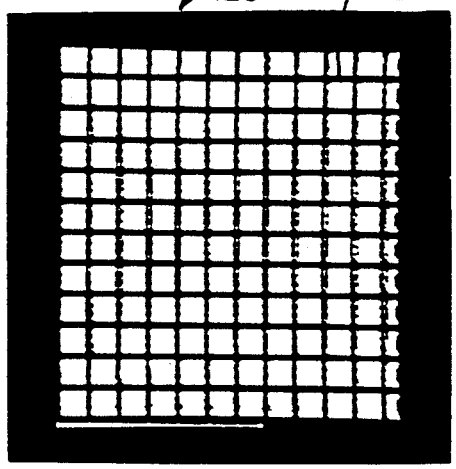
FIG. 6F is a composite image of FIG. 6B superimposed on FIG. 6E illustrating the corrected image of FIG. 6E in comparison with the distorted image of FIG. 6B.

FIG. 6F shows a composite of FIG. 6B and 6E. The difference, now due primarily or entirely to the distortion in FIG. 6B, is about half that of FIG. 6C, as would be expected if the error in the corrected image were negligible. Even if the corrected image in FIG. 6E were completely free of distortion, there should be a difference, between it and FIG. 6B. By comparison with FIG. 6C, it can be seen that the geometrical artifacts have at all points been greatly reduced and essentially eliminated. It is not possible to see from FIG. 6E that the method and apparatus of the present invention also corrects intensity distortions as mentioned above, but it should be understood that such corrections are indeed made using the technique and device of the present invention.

It will be appreciated that the present invention corrects distortions due to field inhomogeneities to a significant degree which is greatly enhanced over that of the prior art methods. Field variations $\Delta B$ are often stated relative to the size of the main field B in p parts per million, where $p=(\Delta B/B)\times 10^6$. For a typical clinical instrument, such as a Siemens Magnetom, $B=1.5$ T, the inhomogeneity can be maintained at $p=7$, over a distance of 20 centimeters. For a typical gradient of about 2.5 mT/m, $\Delta x$ is approximately 0.6p mm. Thus, for the Magnetrom and this gradient an absolute positioning error of $\pm 4.2$ mm is possible. Recently published results of a trial assessment of various MRI systems revealed errors in measuring a 140 mm distance in the frequency encoding direction ranging from 1 mm to 12 mm. This error range is too great for many applications, including stereotactic procedures. The present invention improves the geometrical accuracy of MRI for stereotactic procedures. Stereotactic procedures in the brain, which require positional accuracies of one millimeter or better, place a restriction on the field homogeneity, but they do not require that $|p|$ be kept small enough to keep $|\Delta x| \leq 1$ mm. The restriction need be applied only to part of the inhomogeneity. Because stereotactic positions within the skull are reckoned relative to an external coordinate system rigidly attached to the skull, all spatially uniform translational, rotational, and magnification errors are compensated. This compensation comes about naturally because the coordinate system is itself subject to the same translation, rotation, and magnification as the target. However, all other geometrical distortions, including skew and nonlinear warping are not compensated. It is these residual distortions that must be reduced to one millimeter or less, and it is this requirement that is achieved by the method and related apparatus of the present invention.

For convenience of reference, examples showing the pulse-gradient sequence with $\alpha = -1$ have been given, however as will be known to those skilled in the art, other values for $\alpha$ may be used in accordance with the teachings of the present invention. It should also be appreciated that although the invention has been described with respect to stereotactic neurosurgery, it has application in many different fields such as that of noninvasive industrial testing.

It will be appreciated, therefore, that the present invention provides an effective means for correcting the distortion in images due to magnetic field inhomogeneities and object susceptibility, with a degree of precision allowing for stereotactic accuracy. All of this is accomplished with a fast timing factor and in a reliable, economical and efficient manner.

Whereas particular embodiments of the present invention have been described above for purposes of illustration, it will be appreciated by those skilled in the art that numerous variations of the details may be made without departing from the invention as described in the appended claims.

```
/************************** mri_derive.c **********************
 *
 *
 *
 *
 *
 *
 * Purpose:
 *   This routine takes, as input, two images f'(x,y), and
 *   f''(x'', y'') where f' is from distortion dx, dy=a*dx,
 *   and f'' is from -dx, -dy respectively, and figures out
 *   a third image which is supposed to be free of distortions.
 *
```

```
 * The integration is along a line angled at dy/dx = a, where
 * 'a' is read in from f' file's title field.  The third image is
 * written out into a file as named via the command line.
 */ include <math.h>
include "/nfs/ip3/users/hsc/thesis/jac/jac.h"
#define DIST_PE 0.5
/* not filling for the missing points
#define BLANK_DOT
*/ int total_pix;
GREYTYPE *fx;           /* input /usr/image data holder */
int Int_scheme;
double h;

main(argc,argv)
int argc;
char *argv[];
{
        float g_slope,          /* Gx slope: Delta_y/Delta_x */
              a;                /* Gy = a*Gx: gradient ratio */
        struct imstat stat;
        IMAGE
                *inim,  /* pointer to input f(x, y) /usr/image file       */
                *fpim,  /* pointer to f'(x', y) /usr/image file            */
                *fppim, /* pointer to f''(x'', y) /usr/image file          */
                *ffim;  /* pointer to ff(x, y) /usr/image file             */
        char s[120];
        int i, pixformat, derive_ff();

if(argc<4) errorx("Usage: derive fpim fppim outim [Noise] [H_step]");

if(argc>=5) sscanf(argv[4], "%d", &Noise);
else Noise=0;
if(argc>=6) {
        sscanf(argv[5], "%d", &H_step);
        if(H_step>1) tmp_x2 = (double *)malloc((sizeof(double)+1)*H_step);
        else H_step = 1;
}
else H_step = 1;
h = 1.0/H_step;

/* set up linear interpolation flag. */
/* may have more others in the future */
Int_scheme = L_INTERP;
/* access /usr/image file */
if ((fpim=imopen(argv[1], READ))==INVALID) errorx("can't imopen file");
if (imdim(fpim, &pixformat, &(stat.dimc))==INVALID) errorx("imdim failed");
if (stat.dimc!=2) errorx("Sorry, handle only 2D /usr/image files for now");
if (pixformat!=GREY) errorx("non GREY type image");

/* need to check on the size consistancy of the two input images */
if ((fppim=imopen(argv[2], READ))==INVALID) errorx("can't imopen file");

/* getting the size of image etc from the input file */
stat.endpts= (int *)malloc(sizeof(int)*stat.dimc*2);
stat.dimv  = (int *)malloc(sizeof(int)*stat.dimc);
stat.coarseness = (int *)malloc(sizeof(int)*stat.dimc);
if ((stat.endpts==NULL)|(stat.dimv==NULL)|(stat.coarseness==NULL))
        errorx("malloc failed");
if (imbounds(fpim, stat.dimv)==INVALID) errorx("imbounds failed");
if (imgetdesc(fpim, MINMAX, stat.minmax)==INVALID) errorx("imgetdesc failed");
imWidth = stat.dimv[1];
total_pix = stat.dimv[0]*stat.dimv[1];
fx=(GREYTYPE *)malloc(sizeof(GREYTYPE)*total_pix);
fp  = (double *)malloc(sizeof(double)*total_pix);
fpp = (double *)malloc(sizeof(double)*total_pix);
ff  = (double *)malloc(sizeof(double)*total_pix);
if(fx==NULL || fp==NULL || fpp==NULL || ff==NULL)
        errorx("failed to malloc");

/* now check on the existence of output files */
if ((ffim=imcreat(argv[3], 0666, GREY, 2, stat.dimv))==INVALID)
        errorx("can't imcreat output for output file");

/* getting ready to load in the pixels from the input files */
stat.coarseness[0] = 1; stat.coarseness[1] = 1;
stat.endpts[0] = 0;
stat.endpts[1] = stat.dimv[0] - 1;
stat.endpts[2] = 0;
stat.endpts[3] = stat.dimv[1] - 1;
/* load f' */
if (imgetpix(fpim,stat.endpts,stat.coarseness,(char *)fx) == INVALID)
        errorx("imgetpix failed");
for(i=0; i<total_pix; i++) fp[i] = (double)(fx[i]+0.5);
/* load f'' */
```

```
        if (imgetpix(fppim,stat.endpts,stat.coarseness,(char *)fx) == INVALID)
                errorx("imgetpix failed");
        for(i=0; i<total_pix; i++) fpp[i] = (double)(fx[i]+0.5);
        if(INVALID==imgettitle(fpim, s))
                errorx("Sorry, the first image lacks gradient ratio");
        sscanf(s, "%f", &a);
        if(a<0) errorx("Error: negative gradient ratio");
        fprintf(stderr, "Computing the third image...");
        fflush(stderr);
        /* go calculate the third, distortion free image and put */
        /* the result into a file pointed to by ffim              */
        if(-1==derive_ff(&stat, a, ffim)) errorx("bombs inside derive_ff");

fprintf(stderr, "done.\ntype displaytool -i %s to see result\n", argv[3]);
        imclose(fpim);
        imclose(fppim);
        imclose(ffim);
}

/*
 * this routine derives ff(x) based upon
 * f'(x') and f''(x'') using 1D method.
 * the integration is along a line that has
 * tangent a.
 */
derive_ff(im, a, ffim)
struct imstat *im;    /* pointer to the size etc. of images */
double a;             /* tangent of the line to integrate   */
IMAGE *ffim;          /* pointer to the output file         */
{
        int Valid, i, i1, i2, ii, j, k, X, Y, *x1, right_x, true_x;
        int dist, l;
        double tmp1, tmp2, tmp, y, *x2, *tmp_x, *tmp_f,
                rk4(), rk4_2(), bilinear(), sqrt();

X = im->dimv[1];  /* width of image  */
        Y = im->dimv[0];  /* height of image */
        k = (int)(X*sqrt((double)(1.0+a*a)));
        x1 = (int *)malloc(sizeof(int)*k);
        x2 = (double *)malloc(sizeof(double)*k);
if(x1==NULL || x2==NULL) errorx("malloc failed in derive_ff()");
/* added 7/31/89 for discretization of true_x */
tmp_x = (double *)malloc(sizeof(double)*k);
tmp_f = (double *)malloc(sizeof(double)*k);
if(tmp_x==NULL || tmp_f==NULL) errorx("malloc failed in derive_ff()");
/*
 * this for-loop takes care of the upper-right triangle of the 2D space
 * it enters only when a!=0
 */
if(a!=0.0)
  for(j = 1; j<X; j++) {  /* scan through x axis */
        /* find the starting pixel for f' image */
        i1=j; tmp1 = 0.0;
        while(i1<X && tmp1<Y &&
                bilinear(fp, (double)i1, tmp1, X, Y, &Valid)<=Noise) {
                i1++;
                tmp1 = a*(i1-j);
        }
        /* find the starting pixel for f'' image */
        i2=j; tmp1 = 0.0;
        while(i2<X && tmp1<Y &&
                bilinear(fpp, (double)i2, tmp1, X, Y, &Valid)<=Noise) {
                i2++;
                tmp1 = a*(i2-j);
        }
        /* if the line is empty, go for next one */
        if(i1==X || i2==X) {
                fprintf(stderr, "zero line starting at x=%d\n", j);
                continue;
        }

/*
         * start working on the selected line: matching along
         * both lines while governed by the ODE describing
         * the relationship between two corresponding spins
         * that are kept in x1[k] and x2[k].
         * Using Rouge-Kutta method, x2[k] is found in H_step's
         * as the user desires based upon a given x1[k] via the ODE.
         */
        x1[0] = i1; x2[0] = (double)i2; y=(i1+1-j)*a;
        for(i=i1+1, k=1; i<X && y<Y-1; i++, k++) {
                y = (i-j)*a;
                x1[k] = i;
                tmp1 = bilinear(fp, (double)(i-1), y-a, X, Y, &Valid);
                tmp2 = bilinear(fpp, x2[k-1], a*(x2[k-1]-j), X, Y, &Valid);
                if (Valid && H_step<2 && tmp2>0.0)
                        x2[k] = rk4_2(a, X, Y, j, x2[k-1], (double)(i-1), tmp1/tmp2, 1.0);
```

```
                else if (Valid && H_step>1 && tmp2>0.0) {
                    /* it may take several steps to get x2[k] */
                    int m;
                    double xx, yy;
                    tmp_x2[0] = rk4_2(a, X, Y, j, x2[k-1], (double)(i-1),tmp1/tmp2,h);
                    m=1;
                    while(m<H_step) {
                        xx = i-1+m*h;
                        tmp1 = bilinear(fp, xx, (xx-j)*a, X, Y, &Valid);
                        tmp2 = bilinear(fpp, tmp_x2[m-1], a*(tmp_x2[m-1]-j), X, Y, &Valid);
                        if(!Valid) {
                            tmp_x2[m-1] = -1.0;
                            break;
                        }
                        tmp_x2[m] = rk4_2(a, X, Y, j, tmp_x2[m-1], xx, tmp1/tmp2, h);
                        m++;
                    }
                    x2[k] = tmp_x2[m-1];
                }
                else {
                    fprintf(stderr,
                    "Error: division underflow at pixel (%d,%d), when integrating column %d\n",
                    i, (int)(y+0.5), j);
                    x2[k] = -1.0;
                    break;
                }
            }
            /* the following block uses x1[k] and x2[k] to fill x[] space */
            /* using the middle point equation. NB. x[] may not be contig */
#ifdef BLANK_DOT
            /* non-discretized (black dots) version 7/31 */
            for(i=0; i<k; i++) {
                if(x2[i]<0.0) continue;
                tmp1 = bilinear(fp, (double)(x1[i]), (x1[i]-j)*a, X, Y, &Valid);
                tmp2 = bilinear(fpp, x2[i], (x2[i]-j)*a, X, Y, &Valid);
                if(!Valid) continue;
                tmp = (x1[i]+x2[i])*0.5;
                true_x = (int)((int)((tmp-j)*a+0.5)*X+tmp+0.5);
                if(tmp1==0.0 || tmp2==0.0) ff[true_x] = 0.0;
                else ff[true_x] = 2.0*tmp1*tmp2/(tmp1+tmp2);
            }
#else
            for(i=0; i<k; i++) {
                if(x2[i]<0.0) { tmp_x[i] = -1; continue; }
                tmp1 = bilinear(fp, (double)(x1[i]), (x1[i]-j)*a, X, Y, &Valid);
                tmp2 = bilinear(fpp, x2[i], (x2[i]-j)*a, X, Y, &Valid);
                if(!Valid) { tmp_x[i] = -1; continue; } tmp_x[i] = (x1[i]+x2[i])*0.5;
                if(tmp1==0.0 || tmp2==0.0) tmp_f[i] = 0.0;
                else tmp_f[i] = 2.0*tmp1*tmp2/(tmp1+tmp2);
            }
            /* discretization to avoid blank, unfilled pixels       */
            /* using linear interpolation along the integration line */
            i=0; ii=1;
            while(ii<k) {
                while(tmp_x[ii]<0 && ii<k) ii++;   /* skip thru -1 points */
                if((dist = (int)tmp_x[ii]-(int)tmp_x[i])<1) {
                    i = ii; ii++;
                    continue;
                }
                for(l=0; l<dist; l++) {
                    right_x = (int)tmp_x[i]+l;
                    ff[(int)((int)((right_x-j)*a+0.5)*X+right_x+0.5)] =
                        (tmp_f[ii] - tmp_f[i])*(right_x-tmp_x[i])/
                        (tmp_x[ii]-tmp_x[i])+tmp_f[i];
                }
                i = ii; ii++;
            }
#endif
        }
        /* this for-loop takes care of the lower left triangle of the 2D image */
        for(j = 0; j<Y; j++) {   /* scaning through y axis */
            i1=0; tmp1 = (double)j;
            while(i1<X && tmp1<Y &&
                bilinear(fp, (double)i1, tmp1, X, Y, &Valid)<=Noise) {
                i1++;
                tmp1 = a*i1+j;
            }
            i2=0; tmp1 = (double)j;
            while(i2<X && tmp1<Y &&
                bilinear(fpp, (double)i2, tmp1, X, Y, &Valid)<=Noise) {
                i2++;
                tmp1 = a*i2+j;
            }
            if(i1==X || i2==X) {
                fprintf(stderr, "zero line starting at y=%d\n", j);
                continue;
```

```
}
x1[0] = i1; x2[0] = (double)i2;
y = (i1+1)*a+j;
for(i=i1+1, k=1; i<X && y<Y-1; i++, k++) {
        y = i*a+j;
        x1[k] = i;
        tmp1 = bilinear(fp, (double)(i-1), y-a, X, Y, &Valid);

tmp2 = bilinear(fpp, x2[k-1], a*x2[k-1]+j, X, Y, &Valid);
                if (Valid && H_step<2 && tmp2>0.0)
                        x2[k] = rk4(a, X, Y, j, x2[k-1], (double)(i-1), tmp1/tmp2, 1.0);
                else if (Valid && H_step>1 && tmp2>0.0) {
                        int m;
                        double xx, yy;
                        tmp_x2[0] = rk4(a, X, Y, j, x2[k-1], (double)(i-1),tmp1/tmp2, h);
                        m=1;
                        while(m<H_step) {
                                xx = i-1+m*h;
                                tmp1 = bilinear(fp, xx, xx*a+j, X, Y, &Valid);
                                tmp2 = bilinear(fpp, tmp_x2[m-1], a*tmp_x2[m-1]+j, X, Y, &Valid);
                                if(!Valid) {
                                        tmp_x2[m-1] = -1.0;
                                        break;
                                }
                                tmp_x2[m] = rk4(a, X, Y, j, tmp_x2[m-1], xx, tmp1/tmp2, h);
                                m++;
                        }
                        x2[k] = tmp_x2[m-1];
                }
                else {
                        fprintf(stderr,
                        "Error: division underflow at pixel (%d,%d), when integrating line %d\n",
                        i, (int)(i*a+j+0.5), j);
                        x2[k] = -1.0;
                        break;
                }
        }
#ifdef BLANK_DOT
        for(i=0; i<k; i++) {
                if(x2[i]<0.0) continue;
                tmp1 = bilinear(fp, (double)(x1[i]), (double)(x1[i]*a+j), X, Y, &Valid);
                tmp2 = bilinear(fpp, x2[i], x2[i]*a+j, X, Y, &Valid);
                if(!Valid) continue;
                tmp = 0.5*(x1[i]+x2[i]);
                true_x = (int)(0.5 + (int)(j+(int)(tmp*a+0.5))*X + tmp);
                if(tmp1==0.0 || tmp2==0.0) ff[true_x] = 0.0;
                else ff[true_x] = 2.0*tmp1*tmp2/(tmp1+tmp2);
        }
#else
        for(i=0; i<k; i++) {
                if(x2[i]<0.0) { tmp_x[i]=-1; continue; }
                tmp1 = bilinear(fp, (double)(x1[i]), (double)(x1[i]*a+j), X, Y, &Valid);
                tmp2 = bilinear(fpp, x2[i], x2[i]*a+j, X, Y, &Valid);
                if(!Valid) { tmp_x[i]=-1; continue; }
                tmp_x[i] = 0.5*(x1[i]+x2[i]);

if(tmp1==0.0 || tmp2==0.0) tmp_f[i] = 0.0;
                else tmp_f[i] = 2.0*tmp1*tmp2/(tmp1+tmp2);
        }
        /* discretization to avoid blank, unfilled pixels */
        i=0; ii=1;
        while(ii<k) {
                while(tmp_x[ii]<0 && ii<k) ii++;  /* skip thru -1 points */
                if((dist = (int)tmp_x[ii]-(int)tmp_x[i])<1) {
                        i = ii; ii++;
                        continue;
                }
                for(l=0; l<dist; l++) {
                        right_x = (int)tmp_x[i]+l;
                        ff[(int)((j+(int)(right_x*a+0.5))*X+right_x+0.5)] =
                                (tmp_f[ii] - tmp_f[i])*(right_x-tmp_x[i])/
                                (tmp_x[ii]-tmp_x[i])+tmp_f[i];
                }
                i = ii; ii++;
        }
#endif
}
free(x1); free(x2);

/* down load the intermediate real numbers to GREYTYPE */
/* to write out to a /usr/image format file            */
for(i=0; i<total_pix; i++) fx[i]=(int)(ff[i]+0.5);
if(INVALID==imputpix(ffim, im->endpts, im->coarseness, (char *)fx))
        errorx("imputpix failed to write out *.ff file");
free(fx);
}

/* error exit handling routine */
errorx(s)
char *s;
{
```

```
        fprintf(stderr, "Error: %s\n", s);
        exit(1);
}

/*
 * this routine returns a value at a real address from a 2D array
 * using bilinear interpolation
 */
double bilinear(f, x, y, X, Y, okay)
double *f,          /* pointer to the input array            */
       x, y;        /* location where array value is desired */
int X, Y, *okay;    /* dimension of the 2D array and error flag */
{
        int ix, iy, ix1, iy1;
        double xb, yb;

ix = (int)x; iy = (int)y; ix1 = ix+1; iy1 = iy+1;
        xb = ix1-x; yb = iy1-y;
        x -= ix; y -= iy; *okay = TRUE;
        switch(Int_scheme) {
        case L_INTERP:
                /* bilinear interpolation */
                if(ix1<X && iy1<Y && ix>=0 && iy>=0)
                        return((double)((f[iy*X+ix]*xb + f[iy*X+ix1]*x)*yb+
                                (f[iy1*X+ix1]*x + f[iy1*X+ix]*xb)*y));
                else if(ix1==X && iy1<Y && iy>=0) {
                        return((double)(f[iy*X+ix]*yb+f[iy1*X+ix]*y));
                }
                else if(iy1==Y && ix1<X && ix>=0) {
                        return((double)(f[iy*X+ix]*xb + f[iy*X+ix1]*x));
                }
                else {
                        fprintf(stderr, "Warning: pixel addressing (%d, %d) and (%d, %d)\n",
                                ix, iy, ix1, iy1);
                        *okay = FALSE; return(-1.0);
                }
                break;
        default: fprintf(stderr, "Sorry, illegal mode for bilinear\n");
                exit(0);
                break;
        }
}

/*
 * For ODE like
 *
 *       dy
 *      ----  = dydx(x, y)
 *       dx
 *
 * we have first order solution
 *
 *      y(x+h) = y(x) + dydx(x, y)*h
 *
 * according to the Euler's method.
 *
 * This procedure returns a y value at x + h
 * based upon given function dydx(), y, x,
 *
 * and step size h using the fourth-order
 * Runge-Kutta method.
 *
 * NB. In this application, 1/h is the steps
 * to get y(x+1) from y(x). A single call of the
 * following routine gets y(x+h) where h<1.
 */ double rk4(a, X, Y, j, y, x, dydx_at_x, h)
double a;               /* oblique line ratio   */
int    X,               /* number of columns    */
       Y,               /* number of rows       */
       j;               /* current row index    */
double y,               /* known y value at x   */
       x,               /* x value              */
       dydx_at_x,       /* dydx evaluated at x  */
       h;               /* step size            */
{
        double k1, k2, k3, k4, xh, tmp, tmp2;
        double bilinear();
        int Valid;

xh = x + h*0.5;
        tmp = bilinear(fp, xh, a*xh+j, X, Y, &Valid);
        if (!Valid) return(-1.0);
        k1 = h * dydx_at_x;
        tmp2 = bilinear(fpp, y+k1/2, a*(y+k1/2)+j, X, Y, &Valid);
        if (!Valid || tmp2==0.0) return(-1.0);
        k2 = h * tmp/tmp2;
```

```
        tmp2 = bilinear(fpp, y+k2/2, a*(y+k2/2)+j, X, Y, &Valid);
        if (!Valid || tmp2==0.0) return(-1.0);
        k3 = h * tmp/tmp2;
        tmp2 = bilinear(fpp, y+k3, a*(y+k3)+j, X, Y, &Valid);
        if (!Valid || tmp2==0.0) return(-1.0);
        k4 = h * bilinear(fp, x+h, a*(x+h)+j, X, Y, &Valid)/tmp2;
        return((double) (y+k1/6+k2/3+k3/3+k4/6));
}

/* quick fix for upper-right hand triangle of the 2D image */
double rk4_2(a, X, Y, j, y, x, dydx_at_x, h)
double a;             /* oblique line ratio    */
int    X,             /* number of columns     */
       Y,                /* number of rows        */
       j;                /* current column index */
double y,             /* known y value at x    */
       x,             /* x value               */
       dydx_at_x,     /* dydx evaluated at x   */ h;                    /* step size             */ double k1, k2, k3, k4, xh, tmp, tmp2;
    double bilinear();
    int Valid;

xh = x + h*0.5;
    tmp = bilinear(fp, xh, a*(xh-j), X, Y, &Valid);
    if (!Valid) return(-1.0);
    k1 = h * dydx_at_x;
    tmp2 = bilinear(fpp, y+k1/2, a*(y+k1/2-j), X, Y, &Valid);
    if (!Valid || tmp2==0.0) return(-1.0);
    k2 = h * tmp/tmp2;
    tmp2 = bilinear(fpp, y+k2/2, a*(y+k2/2-j), X, Y, &Valid);
    if (!Valid || tmp2==0.0) return(-1.0);
    k3 = h * tmp/tmp2;
    tmp2 = bilinear(fpp, y+k3, a*(y+k3-j), X, Y, &Valid);
    if (!Valid || tmp2==0.0) return(-1.0);
    k4 = h * bilinear(fp, x+h, a*(x+h-j), X, Y, &Valid)/tmp2;
    return((double) (y+k1/6+k2/3+k3/3+k4/6));
```

What is claimed is:

1. A method for obtaining images of a subject by nuclear magnetic resonance imaging, comprising the steps of:
   providing a static magnetic field with in which said subject is disposed, a source of pulsed RF signals, receiver means for receiving signals from said subject, computer means for receiving said signals from said receiver means and establishing image information related thereto and visual display means for displaying images from said image information;
   performing a plurality of first image generating sequences each including applying to said subject a plurality of RF pulses including an initial RF pulse and a refocusing RF pulse in between which a subsequence of gradient pulses is applied to said subject, including a first slice selection gradient pulse, a first phase-encoding gradient pulse, a first preparation gradient pulse and a first read-out gradient pulse, and receiving a first set of NMR signals produced responsively by said subject in said receiver means;
   processing said first set of NMR signals by said computer means to obtain a first set of image information and storing said first set of image information in said computer means;
   performing a plurality of second image generating sequences each including applying to said subject a plurality of RF pulses including an initial RF pulse and a refocusing RF pulse in between which a subsequence of gradient pulses is applied to said subject, including a second slice selection gradient pulse, a second phase-encoding gradient pulse, a second preparation gradient pulse and a second read-out gradient pulse, with at least one of said second gradient pulses being changed according to a signed ratio applied to the gradient pulse used in said first image generating sequence, said at least one gradient pulse including said second read-out gradient pulse, and receiving a second set of NMR signals produced responsively by said subject in said receiver means,
   processing said second set of NMR signals by said computer means to acquire a second set of image information and storing said second set of image information in said computer means;
   combining said first set of image information and said second set of image information to generate a third set of image information; and
   storing said third set of image information in computer means.

2. The method of claim 1, including said first image generating sequence including
   generating said initial RF pulse while substantially simultaneously applying said first slice selecting gradient pulse;
   subsequently applying said first phase-encoding gradient pulse;
   subsequently applying said first preparation gradient pulse;
   generating said refocusing RF pulse; and
   substantially simultaneously applying said first read-out gradient pulse, while simultaneously receiving said first NMR signal.

3. The method of claim 2, including
   generating as said initial RF pulse of said first image generating sequences a 90° pulse.

4. The method of claim 3, including
   generating as said refocusing RF pulse of said first and second image generating sequences a 180° pulse.

5. A method for obtaining images of a subject by nuclear magnetic resonance imaging, comprising the steps of:
   providing a static magnetic field within which said subject is disposed, a source of pulsed RF signals, receiver means for receiving signals from said subject, computer means for receiving said signals from said receiver means and establishing image information related thereto and visual display means for displaying images from said image information;
   performing a plurality of first image generating sequences each including generating an initial RF pulse which is a 90° pulse while substantially simultaneously applying a first slice selection gradient pulse, and subsequently applying a first phase-encoding gradient pulse, and subsequently applying a first preparation gradient pulse, and generating a refocusing RF pulse which is a 180° pulse, and substantially simultaneously applying a first read-out gradient pulse, while simultaneously receiving a first set of NRM signals produced responsively by said subject in said receiver means;
   processing said first set of NMR signals by said computer means to obtain a first set of image
   storing said third set of image information in said computer means.

6. The method of claim 5, including
   generating as said initial RF pulse for said second image generating sequence a 90° pulse.

7. The method of claim 6, including
   generating as said second refocusing RF pulse a 180° pulse.

8. The method of claim 7, including
   performing said second image generating sequence using a signed ratio having a value equal to minus one.

9. The method of claim 5, including
   performing said first image generating sequence a plurality of times to obtain a first slice image.

10. The method of claim 9, including
    performing said second image generating sequence a plurality of times to obtain a second slice image.

11. The method of claim 10, including
    obtaining a plurality of said first slice images and a plurality of second slice images to obtain a first volume image and a second volume image.

12. The method of claim 11, including
    combining said first volume image and said second volume image to produce a third volume image.

13. The method of claim 12, including
    processing said first set of NMR signals by subjecting said first set of signals to a two-dimensional Fourier Transformation to obtain a first image;
    processing said second set of NMR signals by subjecting said second set of signals to a two-dimensional Fourier Transformation to obtain a second image; and
    obtaining said plurality of said first slice images by varying the frequency of said initial RF pulses applied during each said first image generating sequence and obtaining said plurality of second slice images by varying the frequency of said initial RF 14. The method of claim 13 including transmitting said third image to a visual display means for viewing said image.

15. The method of claim 12 wherein the method is used during a stereotactic neurosurgical procedure.

16. An apparatus for obtaining corrected images of a subject using nuclear magnetic resonance imaging comprising:
    means for generating a static magnetic field;
    means for generating a plurality of RF pulses and for directing said pulses into said subject to produce NMR signals in said subject;
    means for generating a plurality of sequences of magnetic field gradients having means for controlling the orientation, magnitude and direction of said gradients, said means also having means for applying said gradients while a first set of NMR signals is being produced for each sequence generated;
    receiver means for receiving said NMR signals and generating output signals representative of said NMR signals; and
    computer means for processing said output signals to generate image information from one set of NMR signals comprising a first image and image information from another set of NMR signals comprising a second image, whereby image information at a first point in said first image is combined with image information at a second, remote point in said second image to obtain image information for at third point in said corrected image.

17. The apparatus of claim 16 further comprising visual display means operatively associated with said image generating computer means for displaying said images.

18. The apparatus of claim 16, wherein
    said magnetic field gradient sequence generating means has means for generating a phase encoding gradient along a first axis, a slice selecting gradient along a second axis perpendicular to said first axis, and a preparation gradient and a read-out gradient along a third axis which is perpendicular to said first and second axes while said NMR signals are being produced, and said magnetic field gradient sequence generating means also has means for changing at least one said gradient by a signed ratio, and wherein said at least one gradient is said read-out gradient.

19. The apparatus of claim 18 wherein said signed ratio is equal to minus one.

20. The method of claim 4 including said second image generating sequence including
    generating an initial RF pulse for said second image generating sequence while substantially simultaneously applying a second slice selection gradient pulse;
    subsequently applying a second phase-encoding gradient pulse;
    subsequently applying a second preparation gradient pulse;
    generating a second refocusing RF pulse; and
    substantially simultaneously applying a second read-out gradient pulse, with at least one of said gradient pulses being changed according to a signed ratio applied to said respective first gradient pulse and wherein said at least one gradient pulse includes said second read out gradient pulse.

21. The method of claim 20 including
    combining image information at a first point in said first set of image information with image information at a second point in said second set of image information, to produce image information at a third point in said third set of image information, and wherein said second point is a point in said second set of image information which is remote from a point corresponding to said first point in said first set of image information.

22. The method of claim 21 including selecting said first, second and third points respectively based upon the acquired first and second sets of image information and said signed ratio.

23. The method of claim 22 including performing said second image generating sequence using a value for said signed ratio of minus one.

* * * * *

UNITED STATES PATENT AND TRADEMARK OFFICE
CERTIFICATE OF CORRECTION

PATENT NO. : 5,099,208

DATED : March 24, 1992

INVENTOR(S) : J.M. Fitzpatrick and Hsuan Chang

It is certified that error appears in the above-identified patent and that said Letters Patent is hereby corrected as shown below:

In the Abstract, line 19, "sequences" should be --sequence--.

Column 1, line 33, --planes-- should be inserted after "multiple".

Column 2, line 10, "magnet" should be --magnetic field pulses--.

Column 2, line 63, "nd" should be --and--.

Column 4, line 11, --.-- should be inserted after "disposed".

Column 12, line 28, "impefiections" should be --imperfections--.

Column 12, lines 39-40, "udnerstood" should be --understood--.

Claim 3, column 26, line 63, --and second-- should be inserted after "first".

UNITED STATES PATENT AND TRADEMARK OFFICE
CERTIFICATE OF CORRECTION

PATENT NO. : 5,099,208
DATED : March 24, 1992
INVENTOR(S) : J.M. Fitzpatrick and Hsuan Chang It is certified that error appears in the above-identified patent and that said Letters Patent is hereby corrected as shown below:

Claim 5, column 27, line 25, the following should be inserted after "image":

--information and storing said first set of image information in said computer means;
    performing a plurality of second image generating sequences each including generating an initial RF pulse for said second image generating sequence while substantially simultaneously applying a second slice selection gradient pulse with said second slice selection gradient pulse changed according to a signed ratio applied to said first slice selection gradient pulse in said first image generating sequence, and subsequently applying a second phase-encoding gradient pulse, and subsequently applying a second preparation gradient pulse with said second preparation gradient pulse changed according to a signed ratio applied to said first preparation gradient pulse in said first image generating sequence, and generating a second refocusing RF pulse, and substantially simultaneously applying a second read-out gradient pulse with said second read-out gradient pulse changed according to a signed ratio applied to said first read-out gradient pulse in said first image generating sequence, and receiving a second set of NMR signals produced responsively by said subject in said receiver means,
    processing said second set of NMR signals by said computer means to obtain a second set of image information and storing said second set of image information in said computer means;
    combining said first set of image information and said second set of image information to generate a third set of image information; and--.

UNITED STATES PATENT AND TRADEMARK OFFICE
CERTIFICATE OF CORRECTION

PATENT NO. : 5,099,208
DATED : March 24, 1992
INVENTOR(S) : J.M. Fitzpatrick and Hsuan Chang It is certified that error appears in the above-identified patent and that said Letters Patent is hereby corrected as shown below:

Claim 13, column 27, line 66, the following should be inserted after "RF":
--pulses applied during each said second image generating sequence.--

Claim 16, column 28, line 27, "at" should be --a--.

Signed and Sealed this

Fifteenth Day of November, 1994

Attest:

BRUCE LEHMAN

*Attesting Officer*  *Commissioner of Patents and Trademarks*